United States Patent
Harris

(10) Patent No.: US 7,810,767 B1
(45) Date of Patent: Oct. 12, 2010

(54) MEDICAL PROCEDURE ARMREST METHOD AND APPARATUS

(76) Inventor: Dorothy M. Harris, 1001 Pleasant View Rd., Bessemer, AL (US) 35020

( * ) Notice: Subject to any disclaimer, the term of this patent is extended or adjusted under 35 U.S.C. 154(b) by 389 days.

(21) Appl. No.: 11/978,037

(22) Filed: Oct. 29, 2007

(51) Int. Cl.
*B68G 5/00* (2006.01)
*B43L 15/00* (2006.01)
*A47C 7/54* (2006.01)

(52) U.S. Cl. ............... 248/118; 248/121; 248/118.1; 248/118.3; 248/118.5; 297/411.2; 297/411.21; 297/411.33

(58) Field of Classification Search .......... 248/121, 248/125, 129, 118, 118.3, 118.1, 118.5; 128/668, 128/667, 680, 682, 683, 684, 686; 606/201–203; 297/411.2, 411.21, 411.33, 38; 84/238
See application file for complete search history.

(56) References Cited

U.S. PATENT DOCUMENTS

| | | | | |
|---|---|---|---|---|
| 988,923 A * | 4/1911 | Bauerfeind | ............... | 5/646 |
| 4,907,835 A * | 3/1990 | Salters | ............... | 296/1.09 |
| 4,966,340 A * | 10/1990 | Hunter | ............... | 248/125.8 |
| 5,104,073 A * | 4/1992 | VanBeek et al. | ............... | 248/118.3 |
| 5,201,319 A * | 4/1993 | Negishi | ............... | 600/485 |
| 5,462,247 A * | 10/1995 | Aldrich | ............... | 248/118 |
| 5,746,480 A * | 5/1998 | Bonutti | ............... | 297/411.35 |
| 5,906,284 A * | 5/1999 | Hammerstrom et al. | ............... | 211/205 |
| 6,102,344 A * | 8/2000 | Kasvin et al. | ............... | 248/118 |
| 6,419,511 B2 * | 7/2002 | Lizell | ............... | 439/210 |
| 6,764,055 B1 * | 7/2004 | Lee | ............... | 248/451 |
| 7,077,766 B2 * | 7/2006 | Bennett et al. | ............... | 473/448 |
| 2005/0288571 A1 * | 12/2005 | Perkins et al. | ............... | 600/407 |

\* cited by examiner

*Primary Examiner*—J. Allen Shriver, II
*Assistant Examiner*—Christopher Garft

(57) ABSTRACT

A medical procedure armrest includes a base and a post that is attached to and extends upwardly from the base. An upper end of the post supports a blood pressure reading apparatus. A bar has a first end and a second end. A coupler is attached to the first end of the bar. The coupler is attached to the post. A housing has a top wall, a bottom wall and peripheral wall extending between the top and bottom walls. The second end of the bar is coupled to the housing. A cushioning member is attached to an upper surface of the top wall of the housing.

10 Claims, 5 Drawing Sheets

MEDICAL PROCEDURE ARMREST METHOD AND APPARATUS

BACKGROUND OF THE INVENTION

Field of the Invention

The present invention relates to armrest devices and more particularly pertains to a new armrest device for supporting a person's arm while a blood pressure reading is being taken.

SUMMARY OF THE INVENTION

The present invention meets the needs presented above by generally comprising a base and a post that is attached to and extends upwardly from the base. An upper end of the post supports a blood pressure reading apparatus. A bar has a first end and a second end. A coupler is attached to the first end of the bar. The coupler is attached to the post. A housing has a top wall, a bottom wall and peripheral wall extending between the top and bottom walls. The second end of the bar is coupled to the housing. A cushioning member is attached to an upper surface of the top wall of the housing.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
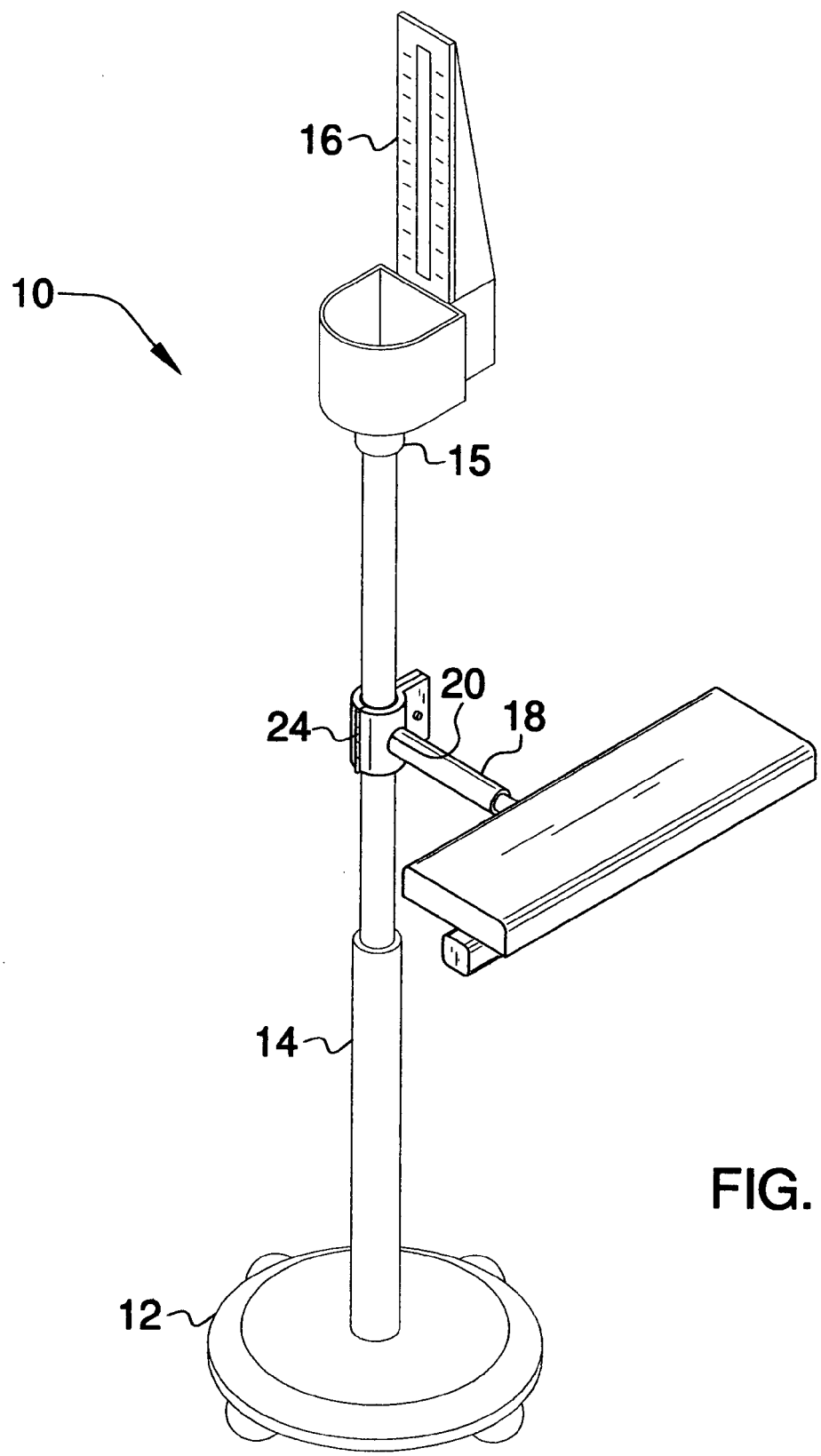
FIG. 1 is a perspective view of a medical procedure armrest method and apparatus according to the present invention.
Figure 2:
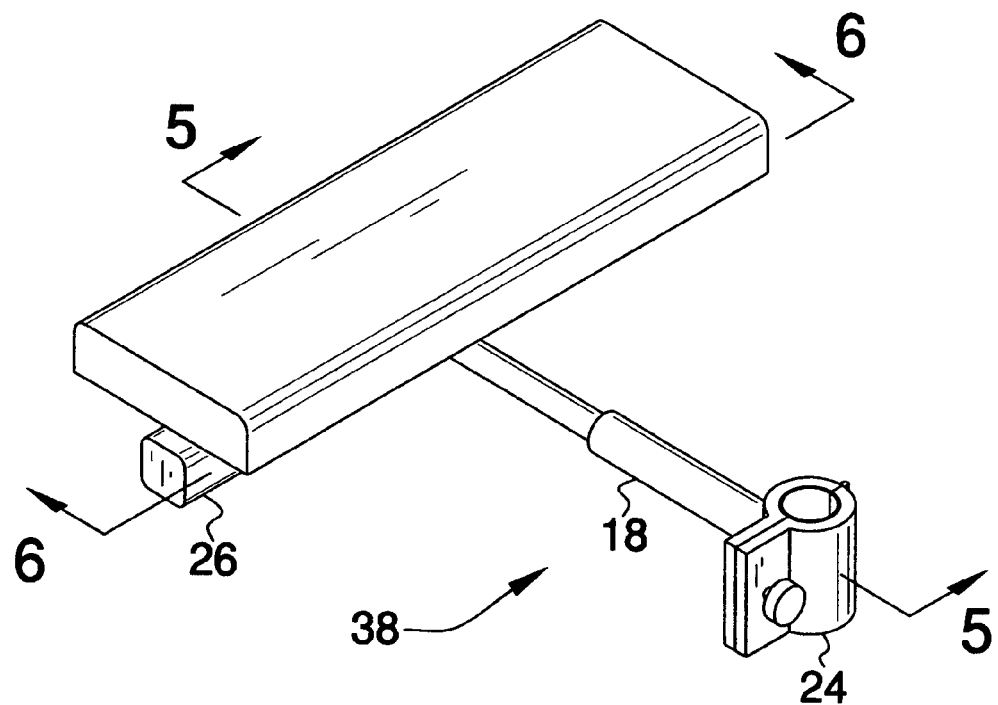
FIG. 2 is a perspective view of arm and housing of the present invention.
Figure 3:
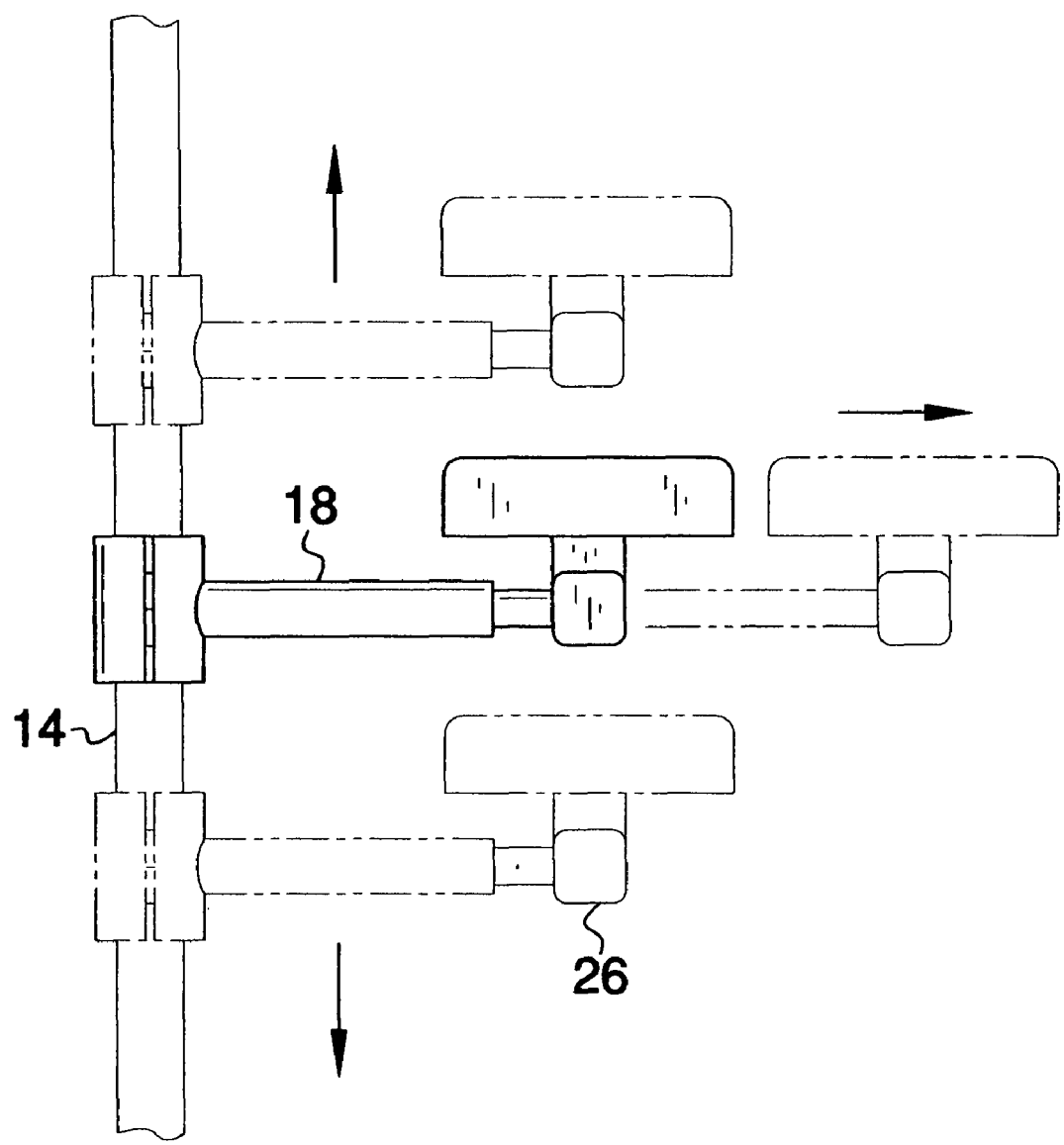
FIG. 3 is a side view of the present invention.
Figure 4:
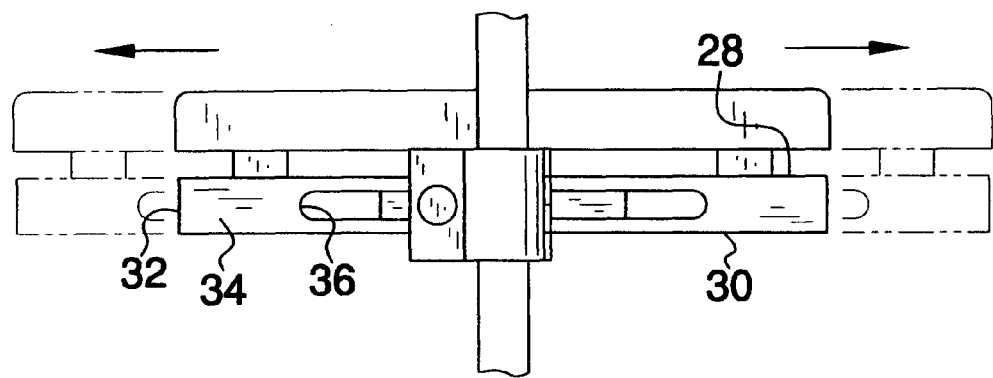
FIG. 4 is a rear view of the present invention.
Figure 5:
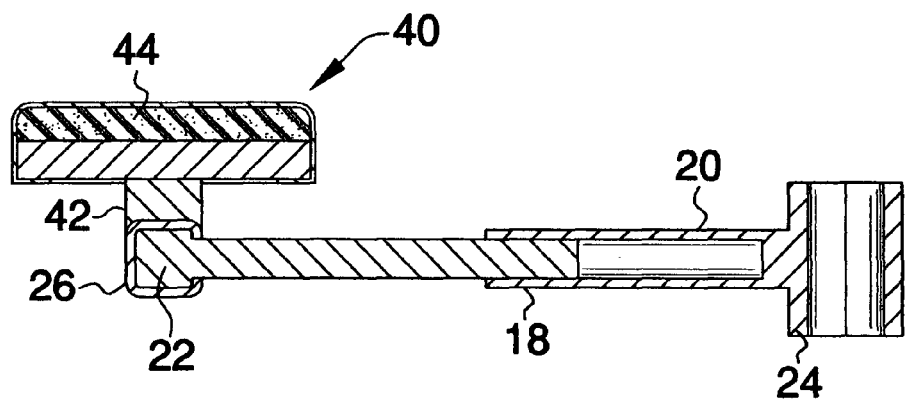
FIG. 5 is a cross-sectional view taken along line 5-5 of FIG. 2 of the present invention.
Figure 6:
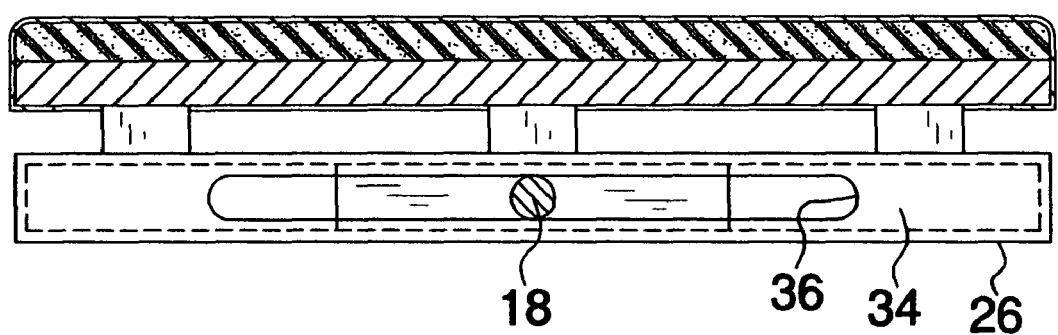
FIG. 6 is a cross-sectional view taken along line 6-6 of FIG. 2 of the present invention.

With reference now to the drawings, and in particular to FIGS. 1 through 6 thereof, a new armrest device embodying the principles and concepts of the present invention and generally designated by the reference numeral 10 will be described.

As best illustrated in FIGS. 1 through 6, the medical procedure armrest method and apparatus 10 generally comprises a base 12 and a post 14 that is attached to and extends upwardly from the base 12. An upper end 15 of the post 14 supports a blood pressure reading apparatus 16 such as a sphygmomanometer.

A bar 18 has a first end 20 and a second end 22. The bar 18 is telescopic and has an alterable length. A coupler 24 is attached to the first end 20 of the bar 18. The coupler 24 is attached to the post 14 and is selectively tightened or loosened with respect to the post 14 to allow a distance between the bar 18 and the base 12 to be adjusted.

A housing 26 has a top wall 28, a bottom wall 30 and peripheral wall 32 extending between the top 28 and bottom 30 walls. The second end 22 of the bar 18 is coupled to the housing 26. The peripheral wall 32 includes an elongated front wall 34 that has an elongated slot 36 therein. The bar 18 extends though the slot 36 to position the second end 22 of the bar 18 within the housing 26. The second end 22 has a size to prevent the second end 22 from being removed through the slot 36. The bar 18 is slidable along the slot 36 to laterally adjust the housing 26 with respect to the bar 18.

A cushioning member 40 is attached to an upper surface of the top wall 28 of the housing 26. The cushioning member 40 includes a plurality of mounts 42 attached to the top wall 28 and a resiliently compressible panel 44 attached to the mounts 42 to position the mounts 42 between the housing 26 and the panel 44. The bar 18, housing 26 and cushioning member 40 define a support 38 for supporting a person's arm.

In use, the arm of a person is positioned on the support 38 while the person is having a blood pressure reading. The support 36 may also be used during blood draws or other procedures. The housing 26 is positioned relative to the post 14 to ensure that the person need be sitting awkwardly or having any stress on the arm while the blood pressure reading is being taken.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An arm supporting apparatus to support an arm while a person is having a blood pressure reading, said apparatus comprising:

a base and a post being attached to and extending upwardly from said base, an upper end of said post supporting a blood pressure reading apparatus;

a bar having a first end and a second end;

a coupler being attached to said first end of said bar, said coupler being attached to said post;

a housing having a top wall, a bottom wall and peripheral wall extending between said top and bottom walls, said second end of said bar being coupled to said housing;

a cushioning member being attached to an upper surface of said top wall of said housing; and said peripheral wall including an elongated front wall having elongated slot therein, said bar extending though said slot to position said second end of said bar within said housing, said second end having a size to prevent said second end from being removed through said slot, said bar being slidable along said slot to laterally adjust said housing with respect to said bar.

2. The arm supporting apparatus according to claim 1, wherein said bar is telescopic and has an alterable length.

3. The arm supporting apparatus according to claim 1, wherein said coupler is selectively tightened or loosened with respect to said post to allow a distance between said bar and said base to be adjusted.

4. The arm supporting apparatus according to claim 1, wherein said cushioning member includes a plurality of mounts attached to said top wall and a resiliently compressible panel attached to said mounts to position said mounts between said housing and said panel.

5. The arm supporting apparatus according to claim 1, wherein said bar is telescopic and has an alterable length.

6. The arm supporting apparatus according to claim 5, wherein said coupler is selectively tightened or loosened with respect to said post to allow a distance between said bar and said base to be adjusted.

7. An arm supporting apparatus to support an arm while a person is having a blood pressure reading, said method comprising:
   a base and a post being attached to and extending upwardly from said base, an upper end of said post supporting a blood pressure reading apparatus;
   a bar having a first end and a second end, said bar being telescopic and having an alterable length;
   a coupler being attached to said first end of said bar, said coupler being attached to said post, said coupler being selectively tightened or loosened with respect to said post to allow a distance between said bar and said base to be adjusted;
   a housing having a top wall, a bottom wall and peripheral wall extending between said top and bottom walls, said second end of said bar being coupled to said housing, said peripheral wall including an elongated front wall having an elongated slot therein, said bar extending though said slot to position said second end of said bar within said housing, said second end having a size to prevent said second end from being removed through said slot, said bar being slidable along said slot to laterally adjust said housing with respect to said bar; and
   a cushioning member being attached to an upper surface of said top wall of said housing, said cushioning member including a plurality of mounts attached to said top wall and a resiliently compressible panel attached to said mounts to position said mounts between said housing and said panel.

8. A method of supporting an arm while a person is having a blood pressure reading, said method comprising:
   providing a base and a post being attached to and extending upwardly from said base, an upper end of said post supporting a blood pressure reading apparatus;
   providing a support including a bar having a first end and a second end, a coupler being attached to said first end of said bar, said coupler being attached to said post, a housing having a top wall, a bottom wall and peripheral wall extending between said top and bottom walls, said second end of said bar being coupled to said housing, a cushioning member being attached to an upper surface of said top wall of said housing, said peripheral wall including an elongated front wall having an elongated slot therein, said bar extending though said slot to position said second end of said bar within said housing, said second end having a size to prevent said second end from being removed through said slot, said bar being slidable along said slot to laterally adjust said housing with respect to said bar; and
   positioning the arm of the person on the support while the person is having a blood pressure reading.

9. The method according to claim 8, wherein the step of providing a support further includes said bar being telescopic and having an alterable length to selectively adjust a distance of said housing from said post.

10. The method according to claim 8, wherein the step of providing a support further includes said coupler being selectively tightened or loosened with respect to said post to allow a distance between said bar and said base to be adjusted.

* * * * *